United States Patent [19]

Behrens et al.

[11] Patent Number: 5,135,934
[45] Date of Patent: Aug. 4, 1992

[54] 3-PHENYL-5,6-DIHYDROBENZ(C) ACRIDINE-7-CARBOXYLIC ACIDS AND RELATED COMPOUNDS AS IMMUNOSUPPRESSIVE AGENTS

[75] Inventors: Carl H. Behrens; Bruce D. Jafee, both of Wilmington, Del.

[73] Assignee: Du Pont Merck Pharmaceutical Company, Wilmington, Del.

[21] Appl. No.: 548,825

[22] Filed: Jul. 6, 1990

[51] Int. Cl.$^5$ ............................................. A61K 31/44
[52] U.S. Cl. ..................................... 514/297; 514/825; 514/855
[58] Field of Search .......................... 514/297, 825, 855

[56] References Cited

U.S. PATENT DOCUMENTS 4,968,701  11/1990  Ackerman et al. ................ 514/312

OTHER PUBLICATIONS

Pharmacological Methods in the control of inflammation, pp. 215-231 (1989), Young et al.

Primary Examiner—Frederick E. Waddell
Assistant Examiner—Zohreh A. Fay
Attorney, Agent, or Firm—Margaret Horn; Blair Q. Ferguson

[57] ABSTRACT

Dihydrobenz[c]acridine carboxylic acid derivatives are provided which are useful for the treatment and/or prevention of organ transplantation rejection, graft versus host disease, autoimmune diseases, psoriasis and chronic inflammatory diseases.

12 Claims, No Drawings

3-PHENYL-5,6-DIHYDROBENZ(C) ACRIDINE-7-CARBOXYLIC ACIDS AND RELATED COMPOUNDS AS IMMUNOSUPPRESSIVE AGENTS

FIELD OF THE INVENTION

This invention relates to methods for the treatment and/or prevention of organ transplantation rejection, graft versus host disease, autoimmune diseases, and chronic inflammatory disease and more particularly to methods of treating such diseases with 3-phenyl-5,6dihydrobenz[c]acridine-7-carboxylic acids and derivatives thereof.

BACKGROUND OF THE INVENTION

Copending and commonly assigned U.S. patent application Ser. No. 07/301,379 now U.S. Pat. No. 4,918,077 and Ser. No. 07/473,507 (Behrens) now U.S. Pat. No. 5,002,954 describe 3-phenyl-5,6-dihydrobenz[c]acridine-7-carboxylic acids and their derivatives as tumor inhibiting agents.

It has now been found that the compounds described in U.S. Ser. No. 07/301,379 now U.S. Pat. No. 4,918,077 and 07/473,507 now U.S. Pat. No. 5,002,954 are useful as immunosuppressive or immunomodulatory agents for the treatment and/or prevention of organ transplantation rejection, graft versus host disease, autoimmune diseases such as rheumatoid arthritis (RA), multiple sclerosis (MS), myasthenia gravis (MG) and systemic lupus erythematosus (SLE), psoriasis and other chronic inflammatory diseases.

The 3-phenyl-5,6-dihydrobenz[c]acridine-7-carboxylic acid compounds of this invention can be used alone or in combination with other known immunosuppressive agents, such as cyclosporin A (CSA), azathioprine (AZA) corticosteroids, OKT3, FK506, mycophenolic acid or the morpholinethylester thereof, 15-deoxyspergualin, rapamycin, mizoribine, misoprostol; or anti-interleukin-2 receptor antibodies, for the treatment and/or prevention of immunomodulatory disorders. When used in combination with other known agents, a lower dose of each agent can be used, with an associated lower incidence of side effects.

SUMMARY OF THE INVENTION

According to the present invention there are provided methods of treating and/or preventing immunologic disorders including autoimmune disease (such as RA, SLE, MS and MG), organ transplantation rejection, graft versus host diseases, psoriasis or other chronic inflammatory diseases in a mammal, said method comprising administering to the mammal an immunosuppressive effective amount of a compound of the formula:

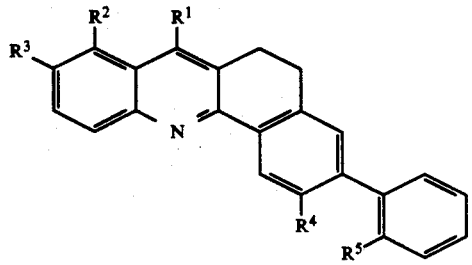

(I)

or a pharmaceutically acceptable salt thereof, wherein
- $R^1$ is $CO_2H$, $CO_2Na$, $CO_2K$ or $CO_2R^6$;
- $R^2$ and $R^3$ independently are H, F, Cl, Br, I, $CH_3$, $CH_2CH_3$, $CF_3$ or $S(O)_mR^7$;
- $R^4$ and $R^5$ independently are H, or taken together are S, with the proviso that when $R^1$ is $CO_2Na$ then $R^3$ is not F;
- $R^6$ is $(CH_2)_nNR^8R^9$;
- $R^7$ is alkyl of 1 to 5 carbon atoms optionally substituted with 1 or 2 of F, Cl and Br;
- $R^8$ and $R^9$ independently are H or alkyl of 1 to 3 carbon atoms;
- m is 0 to 2; and
- n is 2 to 4.

Additionally provided is the above-described method wherein the compound is administered in combination with a non-steroidal anti-inflammatory drug or in combination with at least one immunosuppressive agent selected from the group consisting of cyclosporin A, azathioprine, prednisone, OKT3, FK506, mycophenolic acid or the morpholinethylester thereof, 15-deoxyspergualin, rapamycin, mizoribine, misoprostol and anti-interleukin-2 receptor antibodies. Non-steroidal antiinflammatory agents useful in the present invention include, but are not limited to, aspirin, ibuprofen, naproxen (sodium), indomethocin, suprofen, sulindac, piroxicam and tolmetin sodium.

Current recommended therapy for the prevention of organ transplantation rejection and related disorders, including graft versus host disease, traditionally involves patient treatment with cyclosporin A and adjunct therapy with corticosteroids and other immunosuppressive drugs (Jacobs and Elgin "Cyclosporin A, Current Status, Including the Cape Town Experience" in *Immune Modulation Agents and Their Mechanisms*, ISBN 0-8247-7178-8, 1984, pp 191–228; *Transplantation and Clinical Immunology*, Volume XX, Combined Immunosuppressive Therapy in Transplantation ISBN 0-444-81068-4, 1989). Significant clinically observed toxicities are associated with cyclosporin A (nephrotoxicity) and azathioprine (hepatoxicity).

Our results show that 3-phenyl-5,6-dihydrobenz [c]acridine-7-carboxylic acids and their derivatives should be useful when used alone or included with current regimens of drug therapy for the prevention of organ transplantation rejection and related complications as well as other immunologic diseases.

PREFERRED EMBODIMENTS

Preferred compounds useful in the method of the present invention are those compounds of Formula (I) wherein:
(a) $R^1$ is $CO_2H$ or $CO_2Na$; and/or
(b) $R^2$ is H or Cl; and/or
(c) $R^3$ is H, F, or Cl.

More preferred compounds useful in the method of the present invention are preferred compounds wherein:
(a) $R^2$ is H; and/or
(b) $R^3$ is H or F.

Specifically preferred compounds useful in the method of the present invention are:
(a) 5,6-Dihydro-3-phenylbenz[c]acridine-7-carboxylic acid, or a sodium salt;
(b) 5,6-Dihydro-9-fluoro-3-phenylbenz[c]acridine-7-carboxylic acid, or a sodium salt;

(c) 6,7-Dihydro-3-fluoro-[1]benzothieno[2',3':4,5-]benz[1,2-c]acridine-5-carboxylic acid, or a sodium salt; and (d) 6,7-Dihydro-[1]-benzothieno[2',3':4,5]-benz[1,2-c]acridine-5-carboxylic acid, or a sodium salt.

DETAILED DESCRIPTION OF THE INVENTION

The 3-phenyl-5,6-dihydrobenz[c]acridine-7-carboxylic acids and related compounds useful in this invention are described in and prepared by methods set forth in copending, commonly assigned U.S. patent applications Ser. No. 07/301,379 and Ser. No. 07/473,507 now U.S. Pat. No. 5,002,954 the disclosure, synthesis, and synthetic examples of which are hereby incorporated by reference.

The isolation of the FK506 natural product is described in European Patent Application publication number 240,773, published Oct. 14, 1987 and the chemical synthesis of FK506 is described in Jones et al. (1989) *J. Am. Chem. Soc.* 111:1157-1159.

The preparation of azathioprine is described in U.S. Pat. No. 3,056,785 issued to Burroughs Wellcome. Azathioprine is available as Imuran®, for which the product information, including dosage and administration, is given in *Physicians' Desk Reference* 44th Edition, 1990, pp 777-778.

The preparation of cyclosporin A is described in U.S. Pat. No. 4,117,118 issued to Sandoz. Cyclosporin A is available as Sandimmune®, for which the product information, including dosage and information, is given in *Physicians' Desk Reference*, 44th Edition, 1990, pp 1950-1952.

The preparation of prednisone is described in U.S. Pat. Nos. 2,897,216 and 3,134,718 issued to Schering. Prednisone is available commercially from several manufacturers (see generally, *Physicians' Desk Reference*, supra).

Murine monoclonal antibody to the human T3 antigen (herein referred to as OKT3) is available as Orthoclone OKT®3, for which the product information, including dosage and administration and references to methods of preparation, is given in PDR, 1990, pp 1553-1554.

The preparation of mycophenolic acid is described in British patents 1,157,099; 1,157,100 and 1,158,387 to ICI.

15-deoxyspergualin is a derivative of spergualin discovered in culture filtrates of the bacterial strain BGM 162-aFZ as reported in Ochiai, T., Hoi, S., Nakajimak, et al. Prolongation of Rat Heart Allograft Survival by 15-deoxyspergualin, 5. *Antibiot.* (Tokyo) 987; 40:249.

Mizoribine is described in U.S. Pat. No. 3,888,843 issued to Toyo Jozo.

Misoprostol, a prostaglandin (PGEI) analog, is described in U.S. Pat. No. 3,965,143 assigned to Searle and U.S. Pat. No. 4,132,738 assigned to Miles.

Rapamycin is described in U.S. Pat. Nos. 4,650,803; 4,316,885; 4,885,171; 3,993,749 and 3,929,992 all assigned to Ayerst.

Antibodies to the IL-2 receptor protein are described in U.S. Pat. Nos. 4,578,335 and 4,845,198 (Immunex) and U.S. Ser. No. 07/341,361 still pending and U.S. Pat. No. 4,892,827 issued to Pastan et al.

Utility

Results of the biological tests described below establish that the compounds of this invention have the ability to suppress/inhibit the contact sensitivity response to 2,4-dinitrofluorophenyl (DNFB) in mice and the human mixed lymphocyte reaction.

Contact Sensitivity Response to DNFB in Mice

Balb/c female mice ($\approx$20 g; Charles River) were sensitized on the shaved abdomen with 25 $\mu$l or 0.5% 2,4-dinitrofluorobenzene (DNFB, Eastman Kodak Co.) in a vehicle of 4:1 acetone:olive oil on days 0 and 1. Mice were ear challenged with 20 $\mu$l of 0.2% DNFB in a vehicle of 4:1 acetone:olive oil on day-5. An identical segment of the ear was measured immediately before challenge and 24 hours later with an engineer's micrometer. Ear swelling was expressed as the difference in ear thickness before and after challenge in units of $10^{-4}$ inches $\pm$ SEM. Percent suppression was calculated as:

$$\% \text{ Suppression} = 1 - \frac{\text{compound treated} - \text{negative control}}{\text{positive control} - \text{negative control}} \times 100$$

Compounds were administered orally from day-2 through day-6 and were prepared in 0.25% Methocel® (Dow Chemical Co.). Control animals received only vehicle (0.25% Methocel®). Negative controls were not sensitized on days 0 and 1 but were ear challenged on day-5. Ten mice were used per group. Results with compounds of the present invention are shown in Table 1.

Contact sensitivity to DNFB is a form of delayed-type hypersensitivity which has been extensively studied to gain an understanding of the regulation of immunologic processes (Claman et al. (1980), *Immunological Rev.* 50:105-132). This reaction is mediated by T lymphocytes that become sensitized to antigen by proliferating and developing into mature effector cells (Claman et al. (1980), *Immunological Rev.* 50:105-132). This cell-mediated immune response (T-cell mediated immunity) is central to many disease states such as organ transplantation rejection and graft versus host disease (Benacerraf and Unanue (1979), *Textbook of Immunology*, Williams & Wilkins Co.; Eisen (1980), *Immunology, An Introduction to Molecular and Cellular Principles of the Immune Responses*, Harper & Row, Inc.; Loveland and McKenzie (1982) *Immunology* 46:313-320; Gallin et al. (1988), *Inflammation, Basic Principles and Clinical Correlates*, Raven Press).

The contact sensitivity model used for this study is a model system for delayed-type hypersensitivity reactions which have been linked to the disease pathology associated with organ transplantation rejection, graft versus host disease, MS, MG, SLE, RA, psoriasis and other chronic inflammatory diseases and autoimmune diseases for which the T-cell is pivotal to mounting an immune or autoimmune response.

A representative 3-phenyl-5,6-dihydrobenz[c] acridine-7-carboxylic acid compound of the method of the invention, 5,6-dihydro-9-fluoro-3-phenylbenz-[c]-acridine-7-carboxylic acid, sodium salt (Example 12 of U.S. patent application Ser. No. 07/301,379); herein referred to as Example 12), was tested in the DNFB contact sensitivity model (Table 1).

TABLE 1

| Treatment | Dose (mg/kg) | Ear Swelling[a] (units ± SEM) | % Suppression |
|---|---|---|---|
| Negative | Vehicle | 2.30 ± 0.86 | — |
| Positive | Vehicle | 57.17 ± 3.51 | 0 |
| Cyclosporin A | 20.0 | 41.50 ± 5.85 | 28.55 |
| Example 12 | 20.0 | 2.44 ± 1.62 | 99.75 |

[a]Increase in ear thickness from day 5 to day 6, unit = $10^{-4}$ inches

The present results show that Example 12 and related 3-phenyl-5,6-dihydrobenz[c]acridine-7-carboxylic acid derivatives have immunosuppressive activity and as such should be useful when included alone or in combination with other drugs used in current regimens of drug therapy for the prevention of organ transplantation rejection, autoimmune disease, chronic inflammatory disease, and related disorders (Jacobs and Elgin (1984) "Cyclosporin A, Current Status, Including the Cape Town Experience", in *Immune Modulation Agents and Their Mechanisms*, pp 191–228; *Transplantation and Clinical Immunology*, Volume XX, Combined Immunosuppressive Therapy in Transplantation ISBN 0-444-81068-4, 1989).

Human Mixed Lymphocyte Reaction

Blood was obtained by venipuncture from two non-related human donors. Peripheral blood mononuclear cells (PBMC) were isolated from these samples by using the Leuco Prep procedure (Becton-Dickinson). PBMC were washed twice in phosphate buffered saline (without calcium and magnesium) and the separate cell isolations were adjusted to the appropriate concentrations in media (RPMI 1640) supplemented with 10% human AB serum and 30 µl/ml gentamicin. Cells from donor A ($2 \times 10^5$) were incubated with cells from donor B ($2 \times 10^5$) in 96 well round bottom microliter plates at 37° C., 5% $CO_2$ for 6 days. Eighteen hours prior to harvesting cells from the plates, all wells were pulsed with 1 µCi of $^3$H-thymidine. Cells from the plates were harvested on day-6 and 3H-thymidine incorporation was determined using a scintillation counter. Test results are shown in Table 2.

TABLE 2

| Compound | $IC_{50}$ (M) |
|---|---|
| Cyclosporin A | $1.6 \times 10^{-8}$ |
| Example 12 | $6.5 \times 10^{-8}$ |

The human mixed lymphocyte reaction model, is an in vitro model for transplantation rejection. The results in Table 2 show that Example 12 and related compounds are comparable to CSA the drug of choice for transplantation rejection.

Dosage Forms

The immunosuppressive compounds (active ingredients) of this invention, can be administered to treat immunologic disorders and inflammatory diseases by any means that produces contact of the active ingredient with the agent's site of action in the body of a mammal. They can be administered by any conventional means available for use in conjunction with pharmaceuticals; either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be an immuno-suppressive effective amount of active ingredient and will, of course, vary depending upon known factors such as: the pharmacodynamic characteristics of the particular active ingredient, and its mode and route of administration; age, health, and weight of the recipient; nature and extent of symptoms; kind of concurrent treatment, frequency of treatment; and the effect desired. Usually a daily dosage of active ingredient can be about 0.1 to 400 milligrams per kilogram of body weight. Ordinarily, 1 to 200 and preferably 10 to 50 milligrams per kilogram per day is effective to obtain desired results, provided, that when the compounds of the present invention are used in combination with one or more known immunosuppressive agents, the dose of each agent should be reduced.

Dosage forms (compositions) suitable for internal administration contain from about 1.0 milligram to about 500 milligrams of active ingredient per unit. In these pharmaceutical compositions, the active ingredient will ordinarily be present in an amount of about 0.5–95% weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzaalkonium chloride, methyl- or propyl-paraben, and chlorbutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

Capsules:

A large number of unit capsules are prepared by filling standard two-piece hard gelatin capsules each with 100 milligrams of powdered active ingredient, 175 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 100 milligrams of the active ingredient. The capsules are washed and dried.

Tablets:

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystal line cellulose, 11 milligrams of cornstarch and 98.8 milligrams of lactose. Appropriate coatings may be applied to increase palatability of delay absorption.

Injectable:

A parenteral composition suitable for administration by injection is prepared by stirring 1.5% by weight of active ingredient in 10% by volume propylene glycol and water. The solution is made isotonic with sodium chloride and sterilized.

Suspension:

An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When drugs are administered in physical combination, the dosage form and administration route should be selected for compatibility with both drugs.

What is claimed is:

1. A method of treating graft versus host disease, organ transplantation rejection, or a chronic inflammatory disease in a mammal comprising administering to the mammal in an amount effective for the treatment of a desired aforesaid disease a compound having the formula:

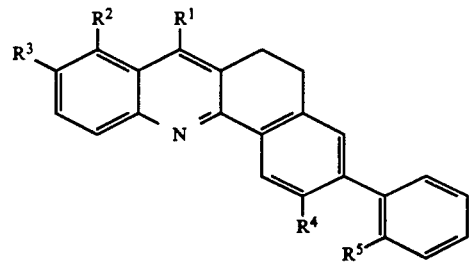

or a pharmaceutically acceptable salt thereof, wherein:
$R^1$ is $CO_2H$, $CO_2Na$, $CO_2K$, or $CO_2R^6$;
$R^2$ and $R^3$ independently are H, F, Cl, Br, I, $CH_3$, $CH_2CH_3$, $CF_3$, or $S(O)_mR^7$;
$R^4$ and $R^5$ independently are H, or taken together are S with the proviso that when $R^1$ is $CO_2Na$ then $R^3$ is not F;
$R^6$ is $(CH_2)_nNR^8R^9$;
$R^7$ is alkyl of 1 to 5 carbon atoms optionally substituted with 1 or 2 of F, Cl and Br;
$R^8$ and $R^9$ independently are H or alkyl of 1 to 3 carbon atoms;
m is 0 to 2; and
n is 2 to 4.

2. A method of claim 1 wherein $R^1$ is $CO_2H$ or $CO_2Na$.

3. A method of claim 1 wherein $R^2$ is H or Cl.

4. A method of claim 1 wherein $R^3$ is H, F or Cl.

5. A method of claim 1 wherein $R^1$ is $CO_2H$ or $CO_2Na$, $R^2$ is H or Cl, and $R^3$ is H, F or Cl.

6. A method of claim 5 wherein $R^2$ is H.

7. A method of claim 5 wherein $R^3$ is H or F.

8. A method of claim 1 wherein $R^2$ is H and $R^3$ is H or F.

9. The method of claim 1 wherein the compound of formula (I) is 5,6-dihydro-3-phenylbenz[c]acridine-7-carboxylic acid, or a sodium salt thereof.

10. The method of claim 1 wherein the compound of formula (I) is 5,6-dihydro-9-fluoro-3-phenylbenz[c]acridine-7-carboxylic acid, or a sodium salt thereof.

11. The method of claim 1 wherein the compound of formula (I) is 6,7-di-hydro-3-fluoro-[1]-benzothieno[2′,3′:4,5]benz[1,2-[c]acridine-5-carboxylic acid, or a sodium salt thereof.

12. The method of claim 1 wherein the compound of formula (I) is 6,7-dihydro-[1]-benzothieno[2′,3′:4,5]benz[1,2-c]acridine-5-carboxylic acid, or a sodium salt thereof.

* * * * *